(12) United States Patent
Forsell

(10) Patent No.: US 11,752,014 B2
(45) Date of Patent: Sep. 12, 2023

(54) APPARATUS AND METHODS FOR TREATMENT OF ARTHROSIS OR OSTEOARTHRITIS IN A JOINT OF A MAMMAL OR HUMAN PATIENT

(71) Applicant: Peter Forsell, Lund (SE)

(72) Inventor: Peter Forsell, Lund (SE)

(*) Notice: Subject to any disclaimer, the term of this patent is extended or adjusted under 35 U.S.C. 154(b) by 290 days.

(21) Appl. No.: 17/167,304

(22) Filed: Feb. 4, 2021

(65) Prior Publication Data
US 2021/0177625 A1   Jun. 17, 2021

Related U.S. Application Data

(63) Continuation of application No. 13/383,368, filed as application No. PCT/SE2010/050818 on Jul. 12, 2010, now abandoned.
(Continued)

(30) Foreign Application Priority Data

| Jul. 10, 2009 | (SE) | 0800975-4 |
| Jul. 10, 2009 | (SE) | 0900957-2 |
| Jul. 10, 2009 | (SE) | 0900958-0 |
| Jul. 10, 2009 | (SE) | 0900959-8 |
| Jul. 10, 2009 | (SE) | 0900960-6 |
| Jul. 10, 2009 | (SE) | 0900961-4 |
| Jul. 10, 2009 | (SE) | 0900962-2 |
| Jul. 10, 2009 | (SE) | 0900963-0 |

(Continued)

(51) Int. Cl.
*A61F 2/30* (2006.01)
*A61B 17/56* (2006.01)
(Continued)

(52) U.S. Cl.
CPC .............. *A61F 2/4618* (2013.01); *A61F 2/30* (2013.01); *A61F 2/30756* (2013.01);
(Continued)

(58) Field of Classification Search
CPC .... A61F 2/30; A61F 2/30756; A61F 2/30942; A61F 2/32; A61F 2/4618;
(Continued)

(56) References Cited

U.S. PATENT DOCUMENTS

2004/0220296 A1* 11/2004 Lowman ................ A61F 2/442
523/113

* cited by examiner

*Primary Examiner* — Samuel S Hanna

(57) ABSTRACT

A proposed treatment of arthrosis/osteoarthritis in a joint of a mammal or human patient involves deposing a liquid material on at least one damaged surface of the joint. To accomplish this, a reservoir (110) is provided, which holds a volume of a biocompatible material in liquid form outside of a body containing the joint (J) to be treated. A proximal end (P) of a tube-shaped instrument (120) is connected to the reservoir (110), and a distal end (D) of the instrument (120) is inserted into the joint (J). The liquid material is fed through the instrument (120) to the distal end (D) for deposition on the at least one damaged joint surface.

The material is configured to assume a solid form under predefined conditions (e.g. when cooling off, or being exposed to a specific type of radiation). When the material has the solid form, it has a resistance to wear adapted to replace a worn out joint surface.

17 Claims, 11 Drawing Sheets

Related U.S. Application Data

(60) Provisional application No. 61/229,745, filed on Jul. 30, 2009, provisional application No. 61/229,752, filed on Jul. 30, 2009, provisional application No. 61/229,767, filed on Jul. 30, 2009, provisional application No. 61/229,778, filed on Jul. 30, 2009, provisional application No. 61/229,730, filed on Jul. 30, 2009, provisional application No. 61/229,733, filed on Jul. 30, 2009, provisional application No. 61/229,789, filed on Jul. 30, 2009, provisional application No. 61/229,748, filed on Jul. 30, 2009, provisional application No. 61/229,743, filed on Jul. 30, 2009, provisional application No. 61/229,747, filed on Jul. 30, 2009, provisional application No. 61/229,811, filed on Jul. 30, 2009, provisional application No. 61/229,735, filed on Jul. 30, 2009, provisional application No. 61/229,802, filed on Jul. 30, 2009, provisional application No. 61/229,739, filed on Jul. 30, 2009, provisional application No. 61/229,738, filed on Jul. 30, 2009, provisional application No. 61/229,751, filed on Jul. 30, 2009, provisional application No. 61/229,731, filed on Jul. 30, 2009, provisional application No. 61/229,796, filed on Jul. 30, 2009, provisional application No. 61/229,746, filed on Jul. 30, 2009, provisional application No. 61/229,761, filed on Jul. 30, 2009, provisional application No. 61/229,815, filed on Jul. 30, 2009, provisional application No. 61/229,816, filed on Jul. 30, 2009, provisional application No. 61/229,786, filed on Jul. 30, 2009, provisional application No. 61/229,755, filed on Jul. 30, 2009, provisional application No. 61/229,805, filed on Jul. 30, 2009.

(30) Foreign Application Priority Data

| Jul. 10, 2009 | (SE) | 0900964-8 |
|---|---|---|
| Jul. 10, 2009 | (SE) | 0900965-5 |
| Jul. 10, 2009 | (SE) | 0900966-3 |
| Jul. 10, 2009 | (SE) | 0900968-9 |
| Jul. 10, 2009 | (SE) | 0900969-7 |
| Jul. 10, 2009 | (SE) | 0900970-5 |
| Jul. 10, 2009 | (SE) | 0900971-3 |
| Jul. 10, 2009 | (SE) | 0900972-1 |
| Jul. 10, 2009 | (SE) | 0900973-9 |
| Jul. 10, 2009 | (SE) | 0900974-7 |
| Jul. 10, 2009 | (SE) | 0900975-4 |
| Jul. 10, 2009 | (SE) | 0900976-2 |
| Jul. 10, 2009 | (SE) | 0900977-0 |
| Jul. 10, 2009 | (SE) | 0900978-8 |
| Jul. 10, 2009 | (SE) | 0900979-6 |
| Jul. 10, 2009 | (SE) | 0900980-4 |
| Jul. 10, 2009 | (SE) | 0900981-2 |
| Jul. 30, 2009 | (WO) | PCT/SE2009/000502 |

(51) Int. Cl.
*A61F 2/46* (2006.01)
*A61B 17/16* (2006.01)
*A61F 2/32* (2006.01)

(52) U.S. Cl.
CPC ....... *A61B 17/1666* (2013.01); *A61B 17/1668* (2013.01); *A61F 2/30942* (2013.01); *A61F 2/32* (2013.01); *A61F 2002/307* (2013.01); *A61F 2002/30065* (2013.01); *A61F 2002/30583* (2013.01); *A61F 2002/30672* (2013.01); *A61F 2002/30754* (2013.01); *A61F 2002/30757* (2013.01); *A61F 2002/465* (2013.01); *A61F 2002/4627* (2013.01); *A61F 2002/4696* (2013.01)

(58) Field of Classification Search
CPC ....... A61F 2002/307; A61F 2002/30754; A61F 2002/30065; A61F 2002/30583; A61F 2002/30672; A61F 2002/465; A61B 17/56; A61B 2017/561; A61B 17/562; A61B 2017/564; A61B 2017/565; A61B 2017/567; A61B 2017/568
See application file for complete search history.

APPARATUS AND METHODS FOR TREATMENT OF ARTHROSIS OR OSTEOARTHRITIS IN A JOINT OF A MAMMAL OR HUMAN PATIENT

This application is a continuation of U.S. application Ser. No. 13/383,368, filed Jan. 10, 2012, which is the U.S. national phase of International Application No. PCT/SE10/50818, filed Jul. 12, 2010, which designated the U.S. and claims the benefit of U.S. Provisional Application Nos. 61/229,733, 61/229,735, 61/229,738, 61/229,739, 61/229,743, 61/229,745, 61/229,746, 61/229,747, 61/229,748, 61/229,751, 61/229,752, 61/229,755, 61/229,761, 61/229,767, 61/229,778, 61/229,786, 61/229,789, 61/229,796, 61/229,802, 61/229,805, 61/229,811, 61/229,815, 61/229,816, 61/229,730, and 61/229,731, all filed on Jul. 30, 2009 and priority from Swedish patent application nos. 0800975-4, 0900980-4, 0900979-6, 0900977-0, 0900975-4, 0900971-3, 0900964-8, 0900961-4, 0900958-0, 0900978-8, 0900976-2, 0900974-7, 0900973-9, 0900972-1, 0900970-5, 0900969-7, 0900968-9, 0900966-3, 0900965-5, 0900963-0, 0900962-2, 0900960-6, 0900959-8, 0900957-2, and 0900981-2, all filed Jul. 10, 2009, the entire contents of each of which are hereby incorporated by reference in this application.

BACKGROUND

The present invention relates generally to surgical treatment of joints. More particularly the invention relates to an apparatus and methods for treatment of arthrosis or osteoarthritis in a joint of a mammal or human patient.

Traditionally, surgical treatment of damaged joint surfaces (for example in the hip or knee joint) has implied a relatively complicated procedure. For example, in case of arthrosis in the hip joint, a substantial portion of the femoral bone is normally replaced with a prosthesis. This type of operation affects comparatively large muscles and/or many ligaments and tendons, which in turn, leads to a long period of convalescence for the patient. Moreover, if only the cartilaginous tissue of the joint is damaged, it is actually unnecessary to remove the healthy femoral bone tissue.

SUMMARY

The object is therefore to alleviate the above problems and provide an uncomplicated solution for treating arthrosis in joints, which minimizes the removal of healthy tissue and decreases the period of convalescence and the pain to the area of the joint.

According to one aspect, an apparatus for treatment comprises: a reservoir configured to hold a volume of a biocompatible material in liquid form having a temperature higher than 100° C. outside of a body containing a joint to be treated, and an instrument having a general tube shape, a distal end of the instrument being configured to be inserted into the joint, a proximal end of the instrument being connected to the reservoir and configured to receive the liquid material there from, the instrument being configured to feed the liquid material having a temperature higher than 100° C. from the proximal end to the distal end for deposition on at least one damaged surface of the joint, such that adjacent nerves are damaged by the heat of the material, the material being configured to assume a solid form under predefined conditions, and when in the solid form the material having a resistance to wear adapted to replace a worn out joint surface.

According to one embodiment, the apparatus further includes a flexible and collapsible mould member. This member has a pre-produced shape adapted to a shape and size of at least one of the at least one damaged surface. Thus, the mould member may contact and cover this joint surface. Additionally, the mould member is configured to be inserted into the joint, and be form-fitted to said damaged surface. The mould member is also configured to be connected to the distal end of the instrument, and when placed in the joint (J) receive the material in liquid form being fed through the instrument. The mould member has an internal volume configured to be filled with liquid material received via the instrument. Moreover, the mould member is configured to enable the predefined conditions for accomplishing a transition from the liquid form to the solid form after that the mould member has been filled with the liquid material.

The mould member is advantageous, since it facilitates targeting a predetermined volume of the liquid material to a specific joint surface both in terms of thickness and lateral coverage.

According to another aspect, the object is achieved by a method for treatment of arthrosis in a joint of a mammal or human patient. The method involves feeding a volume of a bio compatible material in liquid form into a reservoir located outside of a body containing a joint to be treated. The method further involves inserting into the joint an instrument having a general tube shape. A distal end of the instrument is configured to be inserted into the joint, and a proximal end of the instrument is connected to the reservoir. The method further involves receiving the liquid material from the reservoir in the instrument, and feeding the liquid material from the proximal end to the distal end of the instrument. Thereafter, the material is deposed on at least one damaged surface of the joint. Analogous to the above, the material is configured to assume a solid form under predefined conditions, and when in the solid form the material has a resistance to wear adapted to replace a worn out joint surface. In further analogy to the above, irregularities may be repaired on one or both of the opposing surfaces in the joint.

According to yet another aspect, the object is achieved by a surgical method for treatment of arthrosis in a joint of a mammal or human patient. This method involves inserting in a first position an arthroscopic instrument into a joint to be treated. The instrument here includes a camera for viewing the joint. This method further involves providing a reservoir with a volume of a biocompatible material in liquid form outside of a body containing the joint. Moreover, the method involves inserting into the joint an instrument having a general tube shape. A distal end of the instrument is configured to be inserted into the joint, and a proximal end of the instrument is connected to the reservoir. Additionally, the method involves receiving the liquid material from the reservoir in the instrument, and feeding the liquid material from the proximal end to the distal end of the instrument. Then, the material is deposed on at least one damaged surface of the joint. The material is configured to assume a solid form under predefined conditions, and again, when in the solid form the material has a resistance to wear adapted to replace a worn out joint surface. Naturally, here, the camera facilitates execution of the method.

According to a additional aspect, the object is achieved by a surgical method for treatment of arthrosis in a joint of a mammal or human patient. The method involves inserting in a first position an arthroscopic instrument into a joint to be treated. Here, the instrument includes a camera for viewing the joint. The method further involves inserting in at least one second position at least one surgical instrument into the joint. Moreover, the method involves providing a reservoir with a volume of a biocompatible material in liquid form outside of a body containing the joint. The method further involves inserting into the joint an instrument having a general tube shape. A distal end of the instrument is configured to be inserted into the joint, and a proximal end of the instrument is connected to the reservoir. Furthermore, the method involves inserting a mould member into the joint. The mould member has a pre-produced shape adapted to a shape and size of at least one damaged surface of the joint, so as contact and cover this surface when the mould member is placed in the joint. The mould member is also flexible, collapsible and has an internal volume configured to be filled with liquid material received via the instrument. The mould member is connected to the distal end of the instrument. The method further involves form-fitting the mould member to said at least one damaged surface, injecting the material into the mould member through the instrument, and receiving the material in the mould member. Then, after that the mould member has been filled with the liquid material, the material is caused to transition from the liquid form to a solid form. When in the solid form the material has a resistance to wear adapted to replace a worn out joint surface.

Here, the mould member facilitates targeting a predetermined volume of the liquid material to a specific joint surface both in terms of thickness and lateral coverage. Hence, an even better end result may be attained.

According to yet another aspect, the object is achieved by a surgical method for treatment of arthrosis in a joint of a mammal or human patient. The method involves inserting in a first position an arthroscopic instrument into a joint to be treated. Again, the instrument includes a camera for viewing the joint. The method further involves inserting in at least one second position at least one surgical instrument into the joint. A reservoir is provided with a volume of a biocompatible material in liquid form outside of a body containing the joint. The method also involves inserting into the joint an instrument having a general tube shape. A distal end of the instrument is configured to be inserted into the joint, and a proximal end of the instrument is connected to the reservoir. Furthermore, the method also involves inserting a mould member into the joint. The mould member has a pre-produced shape adapted to a shape and size of at least one of the damaged surface, so as contact and cover the damaged surface when the mould member is placed in the joint. Additionally, the mould member is flexible, collapsible and has an internal volume configured to be filled with liquid material received via the instrument. The mould member is connected to the distal end of the instrument. The mould member is also form-fitted to the damaged surface, the material is injected into the mould member through the instrument, the material is received in the mould member. Then, after that the mould member has been filled with the liquid material, the method involves causing a transition of the material from the liquid form to a solid form. When in the solid form the material having a resistance to wear adapted to replace a worn out joint surface.

Preferably, the mould member is designed to be at least partially removed after that the biocompatible material has become solid, and the method involves removing (at least partially) the mould member from the joint at an appropriate stage of the procedure. Alternatively, the mould member may be configured to disintegrate automatically, e.g. in connection with the material becoming solid.

According to still another aspect, the object is achieved by a method for surgically placing the above-proposed apparatus in a patient via a laparoscopic abdominal approach. The method involves inserting a tube-shaped instrument into the abdomen of the patient's body. The method also involves supplying gas into the patient's abdomen via the tube-shaped instrument, so as to expand the patient's abdominal cavity. At least two laparoscopic trocars are placed in the patient's body, and a camera is inserted through one of the laparoscopic trocars into the patient's abdomen. Additionally, the method involves inserting at least one dissecting tool through one of the at least two laparoscopic trocars. The method further involves dissecting a bone area opposite to the hip region. At least one hole is drilled in the bone of the patient from the abdomen reaching the hip joint, and through this at least one hole surgery and treatment are performed for treating arthrosis or osteoarthritis of the hip by using the proposed apparatus. This approach is advantageous, since it provides convenient access to the hip joint, while leaving the musculature surrounding the hip joint essentially intact.

According to a further aspect, the object is achieved by a method for surgically placing the above-proposed apparatus in a patient via a femoral bone approach. This method involves cutting the patient's skin at the lateral upper femoral region, and drilling at least one hole in the bone of the patient through the upper femoral region reaching the hip joint. Surgery and treatment for treating arthrosis or osteoarthritis of the hip is then performed through this at least one hole by using the proposed apparatus. Hence, a damaged hip joint can be treated in a very straightforward manner, which causes a low degree of discomfort to the patient. Also in this case, the musculature surrounding the hip joint is at most insignificantly influenced.

In any of the embodiments the material could comprise at least one material selected from the group consisting of: polytetrafluoroethylene, perfluoroalkoxy, fluorinated ethylene propylene, polyethylene, and acrylic polymer mixed with alumina trihydrate.

One advantage is that very small incisions is required. Thus, the healing process after the surgery can be made relatively short. Moreover, no healthy bone tissue is removed unnecessarily. Further advantages, beneficial features and applications will be apparent from the following description and the dependent claims.

BRIEF DESCRIPTION OF THE DRAWINGS

Embodiments are now to be explained more closely, which are disclosed as examples, and with reference to the attached drawings.

DETAILED DESCRIPTION

Figure 1:
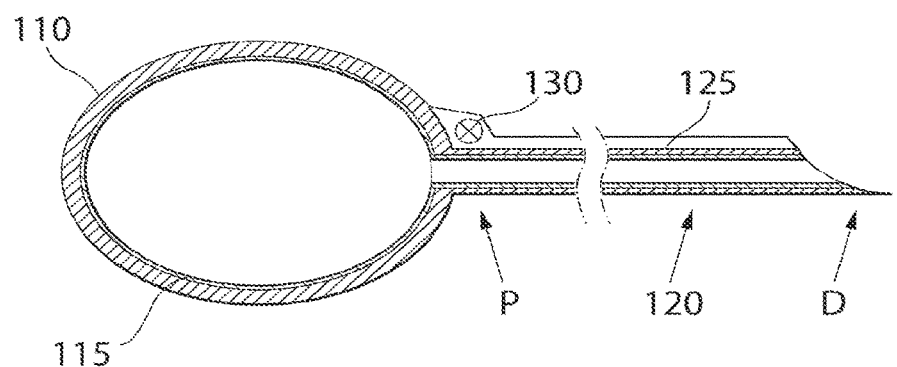
FIG. 1 schematically illustrates an apparatus according to one embodiment.

We refer initially to FIG. 1, which schematically illustrates an apparatus for treatment of arthrosis in a joint according to one embodiment. Typically, the joint is included in a human patient. However, technically, any other mammal may equally well be treated by means of this apparatus, e.g. a horse.

The apparatus includes a reservoir 110 and an instrument 120. The reservoir 110 is configured to hold a volume of a biocompatible material in liquid form outside of a body containing a joint to be treated. The biocompatible material in the reservoir 110 is initially liquid. However, under predefined conditions the material is configured to assume a solid form. For instance, the material may be liquid when its temperature is above a certain level, and solid otherwise; or it may be liquid until it is exposed to a specific type of radiation, say ultraviolet light. These aspects will be elaborated below. In any case, when in the solid form the material has a resistance to wear adapted to replace a worn out joint surface.

The instrument 120 has a general tube shape, which may be substantially more elongated than what is apparent from the examples shown in FIG. 1. The instrument 120 may also be articulated (i.e. including one or more links), so as to enable a more convenient access to joint surfaces inside the body. Irrespective of the length and specific design of the instrument 120, a distal end D thereof 120 is configured to be inserted into the joint to be treated. A proximal end P of the instrument 120 is connected to the reservoir 110 and configured to receive the material in liquid form from the reservoir 110. The instrument 120 is further configured to feed the liquid material from the proximal end P to the distal end D, such that the material can be deposed on at least one damaged joint surface. This instrument could also be inserted into the joint via an arthroscopic trocar i.e. inside another tube, wherein the end of the instrument could be more flat.

According to one embodiment, it is presumed that the biocompatible material in the reservoir 110 is liquid because it has an elevated temperature (i.e. above 37 degrees Celsius), say 50, 70, 90, 100, 150, 200, 300 or 400 degrees Celsius, or any other temperature within an interval from 37 to 500 degrees Celsius. Therefore, the reservoir 110 is configured to hold the biocompatible material at the temperature in question, i.e. 50, 70, 90, 100, 150, 200, 300, 400 degrees Celsius or more. To this aim, the reservoir 110 preferably includes at least one shield member 115, which is configured to isolate the reservoir 110 from the patient's body. Naturally, if the biocompatible material in the reservoir 110 is hot, the material will be hot also when passing through the instrument 120. Hence, the instrument 120 preferably likewise includes at least one shield member 125 configured to isolate the body from liquid material. The material being injected at a high temperature will damage the adjacent nerves, thereby reducing the pain to the area of the joint. Suitable biocompatible materials being liquid at an elevated temperature, and that become solid when cooling off, may comprise fluoropolymers, e.g. in the form of polytetrafluoroethylene, perfluoroalkoxy and/or fluorinated ethylene propylene.

According to another embodiment, it is presumed that the biocompatible material in the reservoir 110 contains two different components. Each of these components is liquid when isolated from the other component. However, when the components are mixed in predefined proportions they develop a solid material. Hence, the two components may represent a hardenable component and a hardening agent respectively. In this embodiment, the reservoir 110 is configured to hold the two components separated from one another during an initial phase of a treatment. During a surgery phase subsequent to the initial phase, the reservoir 110 is configured to mix the two components into a mix. Here, the components are mixed in such proportions that the mix remains liquid during a period required to feed the mix through the instrument 120 to the at least one damaged joint surface in the joint to be treated. Moreover, the instrument 120 is configured to enable such a conveying of the mix.

According to another embodiment, it is presumed that the biocompatible material in the reservoir 110 is liquid due to the fact that the material has not yet been exposed to a specific type of radiation. For example, the material is configured to be liquid if it has been exposed to electromagnetic radiation whose intensity in a predefined spectrum is below a first predefined energy level per unit volume; and the material is configured to be solid if it has been exposed to electromagnetic radiation whose intensity in the predefined spectrum is above a second predefined energy level per unit volume. Here, the apparatus includes an electromagnetic radiation source, which is configured to convey electromagnetic radiation in the predefined spectrum to the at least one damaged joint surface via the instrument 120. Thus, by activating the radiation source after deposition of biocompatible material on the joint surface, the material may be caused to transition from the liquid form to a solid form.

According to another embodiment, it is presumed that the biocompatible material in the reservoir 110 is liquid due to the fact that the material has not yet been exposed to a specific type of mechanical energy. For example, the biocompatible material may be configured to be liquid when it has been exposed to ultrasonic energy in a predefined spectrum whose intensity is below a first predefined energy level per unit volume; and be solid when it has been exposed to ultrasonic energy in the predefined spectrum above a second predefined energy level per unit volume. Here, the apparatus includes an ultrasound source configured to convey ultrasonic energy in the predefined spectrum to the at least one damaged joint surface via the instrument 120. Thus, by activating the ultrasound source after deposition of biocompatible material on the joint surface, the material may be caused to transition from the liquid form to a solid form.

Preferably, since the biocompatible material will be deposed in a patient's body, the reservoir 110 and the connection between the reservoir 110 and the instrument 120 are configured to maintain the material sterile throughout the entire procedure.

Furthermore, according to all aspects, it is advantageous if the apparatus includes a light source 130 configured to illuminate the joint being treated during deposition of the liquid material on at least one damaged surface of this joint.

Figure 2:
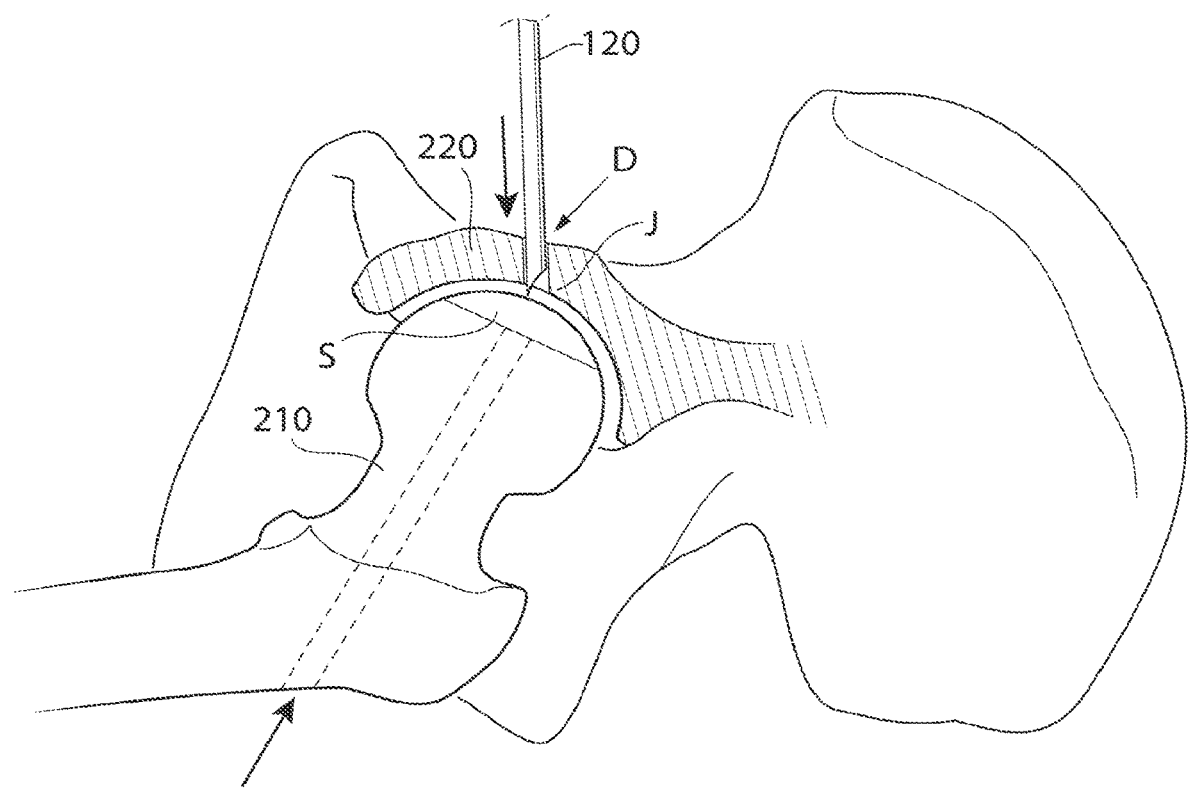
FIG. 2 illustrates how the hip joint of a patient may be reached according to two embodiments.

FIG. 2 illustrates how a damaged surface S of the hip joint J of a patient is reached according to two embodiments. In both cases the joint J is accessed through at least one bone of the body, namely either by passing via the femoral bone 210 or the pelvis bone 220

For example, the distal end D of the proposed instrument 120 may be inserted into the hip joint J by passing via the pelvis bone 220 from inside the abdomen, as illustrated to the right. Here, for reasons of clarity, FIG. 2 only shows the distal-most end D of the instrument 120 as a straight segment. However, of course, in order to reach the joint J, the instrument 120 may be provided with one or more links (not shown). According to one aspect, the apparatus is surgically placed in the patient via a laparoscopic abdominal approach, shown in FIG. 6. Specifically, this involves inserting the tube-shaped instrument 120 into the abdomen of the patient's body. Gas is then supplied into the patient's abdomen via the instrument 120, so as to expand the abdominal cavity. At least two laparoscopic trocars are placed in the patient's body, and a camera is inserted through one of the laparoscopic trocars into the patient's abdomen. Moreover, at least one dissecting tool is inserted through one of the at least two laparoscopic trocars. The method further involves dissecting a bone area opposite to the hip region, and drilling at least one hole in the bone of the patient from the abdomen reaching the hip joint, e.g. as illustrated in FIG. 2. Surgery and treatment for treating arthrosis or osteoarthritis of the hip joint J is then performed through this hole by using the proposed apparatus.

Alternatively, the distal end D of the proposed instrument 120 may be inserted into the hip joint J by passing via the femoral bone 210 of the body, as illustrated to the left in FIG. 2. According to one aspect, the apparatus is surgically placed in the patient via a femoral bone approach, which involves the following. The patient's skin is cut at the lateral upper femoral region. Then, at least one hole is drilled in the bone of the patient through the upper femoral region reaching the hip joint J. Finally, surgery and treatment is performed through this at least one hole for treating arthrosis or osteoarthritis of the hip joint J by using the proposed apparatus.

Preferably, the step of drilling the at least one hole in the bone involves drilling the hole in such a way that a plug of bone is detached into the abdomen. Prior to completing the operation, the method further comprises replacing the plug.

The instrument 120 may also be configured to be inserted into the joint J by passing via a capsula of the joint J.

Irrespective of how the joint J is accessed for treatment of arthrosis therein, according to these embodiments, the method involves the following. A volume of a bio compatible material in liquid form is fed into the reservoir 110 of the apparatus. The reservoir 110 is located outside of a body containing a joint J to be treated. Then, the distal end D of the instrument 120 is inserted into the joint J, and the proximal end P of the instrument 120 is connected to the reservoir 110. Subsequently, the liquid material from the reservoir 110 is received in the instrument 120. Thereafter, the liquid material is fed from the proximal end P to the distal end D of the instrument 120, such that the material is deposed on at least one damaged surface S of the joint J. Finally, the material is caused to transition from the liquid form to a solid form. When in the solid form, the biocompatible material has a resistance to wear adapted to replace a worn out joint surface. Namely, the material is configured to assume the solid form under predefined conditions, for instance in response to a temperature drop, or exposure to radiation.

Figure 3:
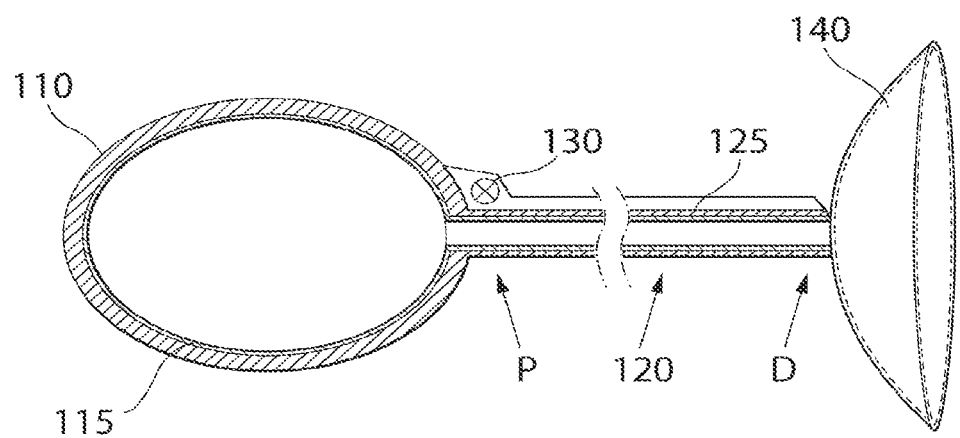
FIG. 3 schematically illustrates how a mould member adapted to a first joint surface is connected to the proposed apparatus according to a first embodiment.

FIG. 3 schematically illustrates how a mould member 140 adapted to a convex joint surface is connected to the proposed apparatus according to one embodiment.

In addition to the embodiment shown in FIG. 1, the apparatus of FIG. 3 includes a flexible and collapsible mould member 140. This member 140 has a pre-produced shape adapted to a shape and size of at least one damaged surface of a specific joint, for instance the surface S of the femoral head represented in FIG. 2. The shape and size of the at least one damaged surface may be determined via a magnetic resonance imaging investigation, a computer tomography x-ray investigation and/or via arthroscopy. The pre-produced shape of the mould member 140 renders it adapted to contact and cover the joint surface S.

Moreover, the mould member 140 is configured to be inserted into the joint J in question and be form-fitted to the damaged surface S. Depending on the location and type of joint, fitting the mould member 140 to the surface S may require a number of additional instruments (not shown). In any case, the mould member 140 is configured to be connected to the distal end D of the instrument, 120 and when placed in the joint J, receive the material in liquid form being fed through the instrument 120. The mould member 140 has an internal volume that is configured to be filled with liquid material received via the instrument 120. Furthermore, after that the mould member 140 has been filled with the liquid biocompatible material, the mould member 140 is configured to enable the predefined conditions, which are required to accomplish a transition of the biocompatible material from the liquid form to the solid form.

Analogous to the embodiments described above with reference to FIG. 1, the apparatus preferable includes a light source 130, e.g. arranged in the instrument 120, configured to illuminate the joint being treated during deposition of the liquid material in the mould member 140.

It is further advantageous if an arthroscopic instrument being inserted into the joint along with the instrument 120 includes a camera for viewing the joint.

Equivalent to the instrument 120 as such, the mould member 140 is configured to be inserted into the joint J by passing via a bone 210 or 220 of the body. This may involve passing via a bone of the body from inside the abdomen, or passing via the femoral bone of the body.

According to some embodiments, the mould member 140 is preferably adapted to be withdrawn (at least partly) from the joint J after that the biocompatible material has assumed its solid form.

Figure 4:
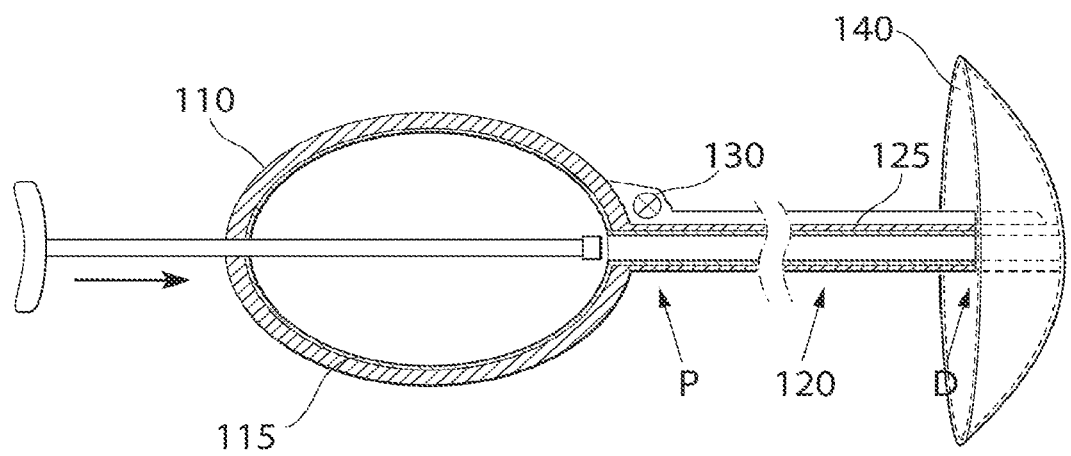
FIG. 4 schematically illustrates how a mould member adapted to a second joint surface is connected to the proposed apparatus according to a second embodiment.

FIG. 4 schematically illustrates how a mould member 140 having a pre-produced shape adapted to a concave joint surface is connected to the proposed apparatus according to one embodiment. Here, all reference signs which also occur in FIG. 1 or 3 designate the same components/features as those described above with reference to these figures.

According to one embodiment, the reservoir 110 is configured to hold the material at an elevated pressure level exceeding the normal atmospheric level. Thus, the mould member 140 may expand in response to receiving the material. Naturally, this is applicable to any configuration of the proposed mould member (i.e. not just the specific design shown in FIG. 4).

Additionally, the apparatus may include an injection member 150 configured to inject the liquid material into the mould member 140 at the elevated pressure. Specifically, the material is injected into the mould member 140 through the instrument 120. When the mould member 140 has been filled with liquid material, this material is caused to transition from the liquid form to the solid form.

Figure 5:
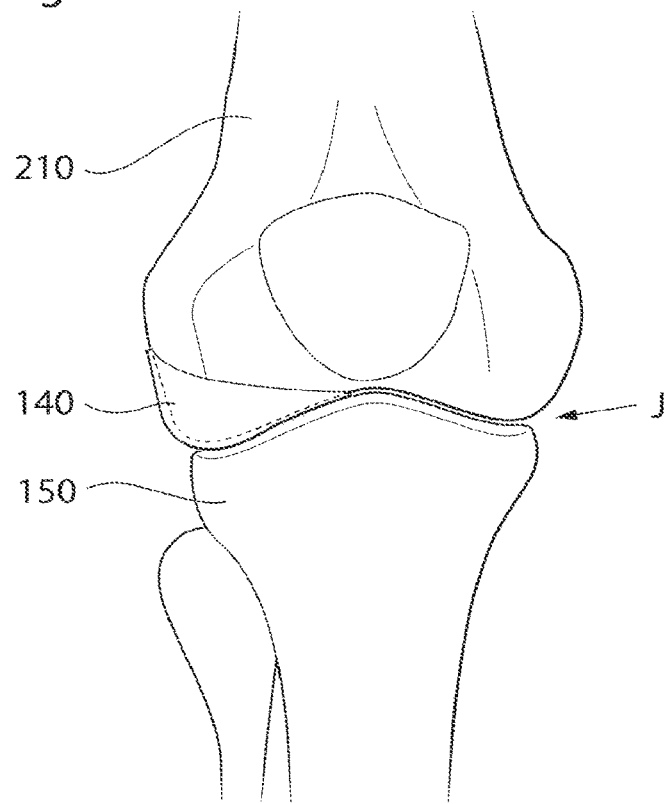
FIG. 5 illustrates how the knee joint of a patient may be treated according to one embodiment.

FIG. 5 illustrates how the knee joint J of a patient may be treated according to one embodiment. Here, a mould member 140 is form-fitted to one of the joint surfaces of the femur bone facing the tibia bone 510, for instance by means of the apparatus shown in FIG. 3.

Preferably, in this case, the distal end D of the instrument 120 is configured to be inserted into the joint J by passing via a capsula of the joint J.

Figure 6:
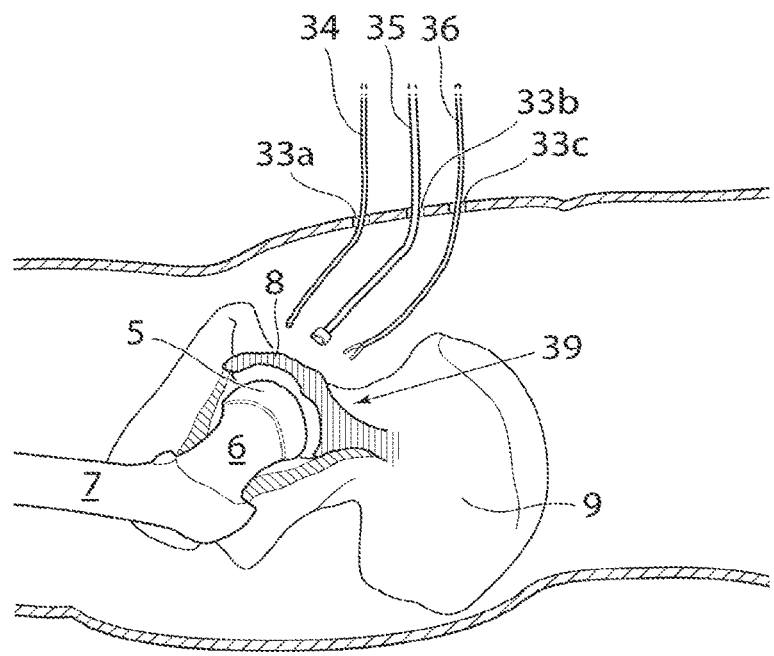
FIG. 6 illustrates how laparoscopic/arthroscopic trocars are approaching the hip joint from the abdominal side of the pelvic bone.

FIG. 6 shows a lateral view of the body of a human patient, with the hip joint shown in section. The hip joint comprises a caput femur 5 placed at the very top of collum femur 6 which is the top part of the femur bone 7. The caput femur 5 is in connection with the acetabulum 8 which is a bowl shaped part of the pelvic bone 9. Laparoscopic/Arthroscopic trocars 33a,b,c is being used to reach the hip joint 39 with one or more camera 34, a surgical instrument 35 adapted to create a hole in the pelvic bone 9, or instruments 36 for introducing, placing, connecting, attaching, creating or filling a mould or an injected fluid.

Figure 7:
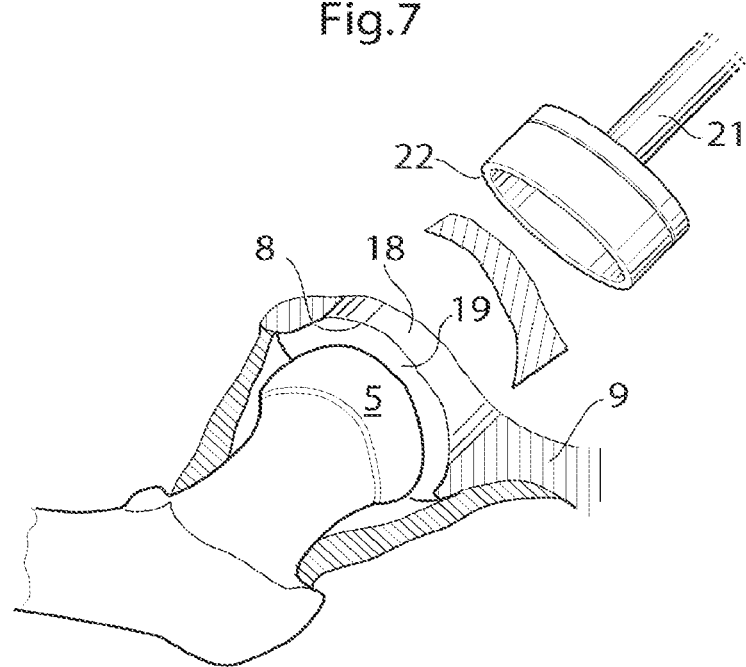
FIG. 7 illustrates how a hole is being created in the pelvic bone from the abdominal side thereof.

FIG. 7 shows an embodiment, wherein the mould is to be used for resurfacing the hip joint. For placing the mould in the hip joint the hip joint needs to be reached, this could be through a hole placed in the pelvic bone 9, the femoral bone 7 or the hip joint capsule 12. FIG. 7 shows the hole 18 in the pelvic bone 9 according to a first embodiment, the hole 18 is large which allows the mould to pass through said hole 18 in its full functional size.

Figure 8:
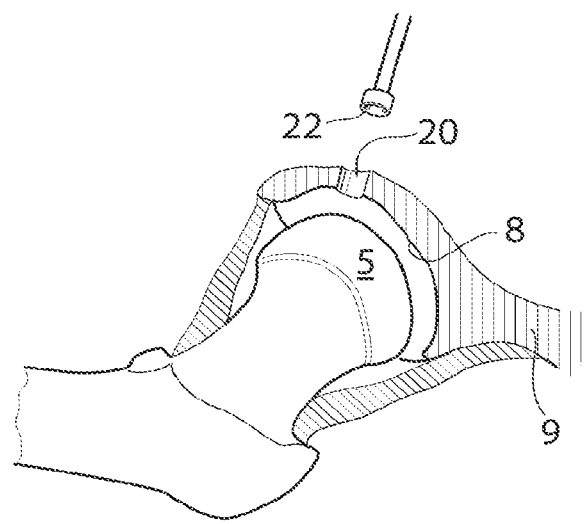
FIG. 8 illustrates how a small hole is being created in the pelvic bone from the abdominal side thereof.

FIG. 8 shows the hole 20 according to a second embodiment wherein the hole 20 created in a surgical or laparoscopic method is much smaller allowing the surgical instrument creating the hole to be smaller, and thus the incision and dissection performed in the human body. To place the mould in the joint in this embodiment the mould needs to be flexible or collapsible.

Figure 9:
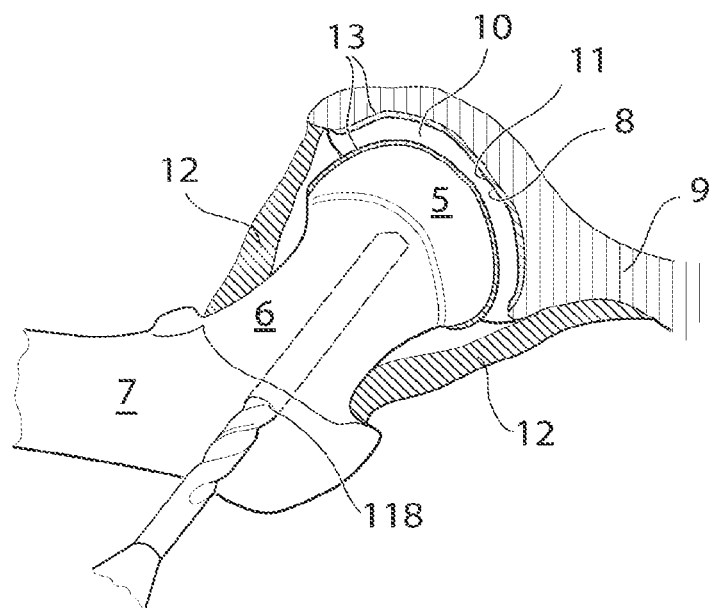
FIG. 9 illustrates how a hole is being created in the femoral bone from the lateral side of the patient.

FIG. 9 shows the hip joint in section when creating a hole in the femur bone 7. The hole in the femur bone passes through the caput femur 5 into the hip joint and enables the surgeon to reach the hip joint.

Figure 10:
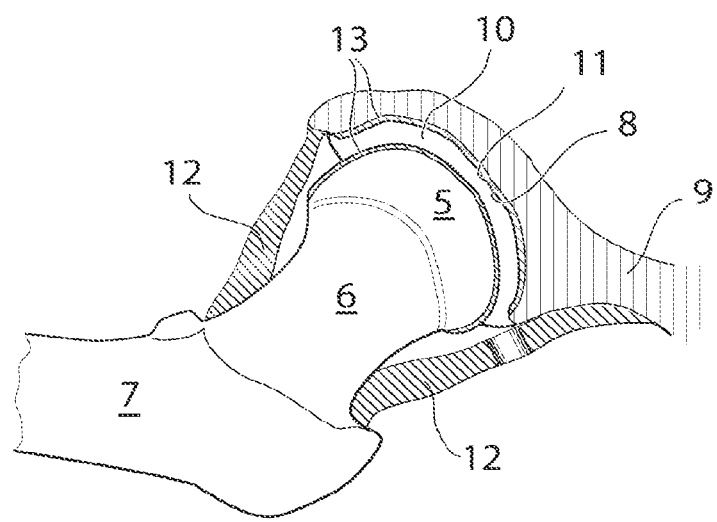
FIG. 10 illustrates how a hole has been created in the hip joint capsule.

FIG. 10 shows the hip joint in section when creating a hole in the hip joint capsule 12. The hole in the hip joint capsule passes into the hip joint and enables the surgeon to reach the hip joint.

Figure 11A:
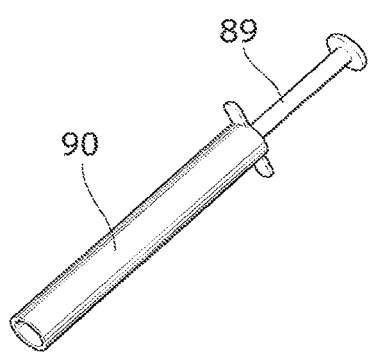
FIG. 11a shows a mould placing instrument.

FIG. 11a shows an instrument for placing a mould 81 in the hip joint or the knee joint through a hole in the pelvic bone, the femur bone, the hip joint capsule or an area of the knee. The instrument comprises a piston 89 for transporting the mould 81 into the joint.

Figure 11B:
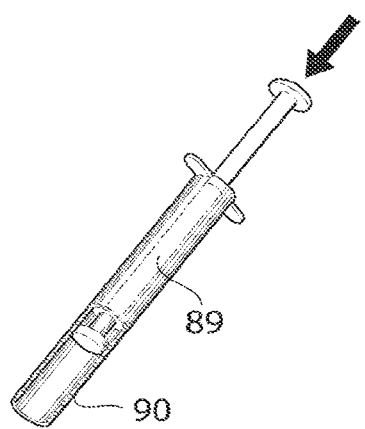
FIG. 11b shows a mould placing instrument.

FIG. 11b shows a section of the surgical instrument comprising a tube like element 90 for housing of said mould 81.

Figure 11C:
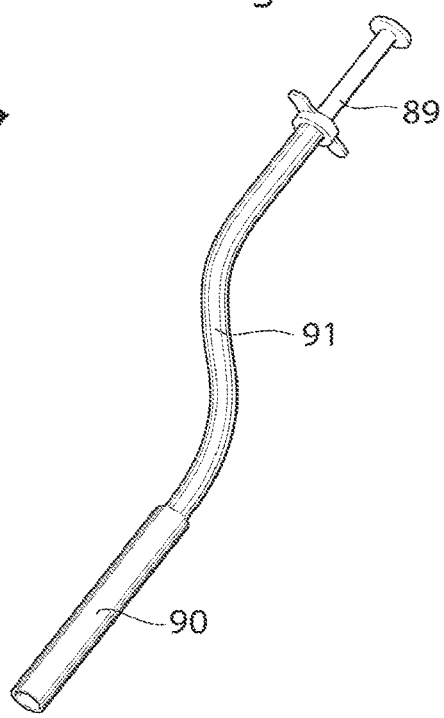
FIG. 11c shows a mould placing instrument.

FIG. 11c shows the surgical instrument according to another embodiment in which the surgical instrument comprises a flexible or bent part 91 improving the reach of the surgical instrument. The surgical instrument according to any of the embodiments can be used to place said mould 81 inside of a joint in any of the ways described in the following embodiments.

Figure 12:
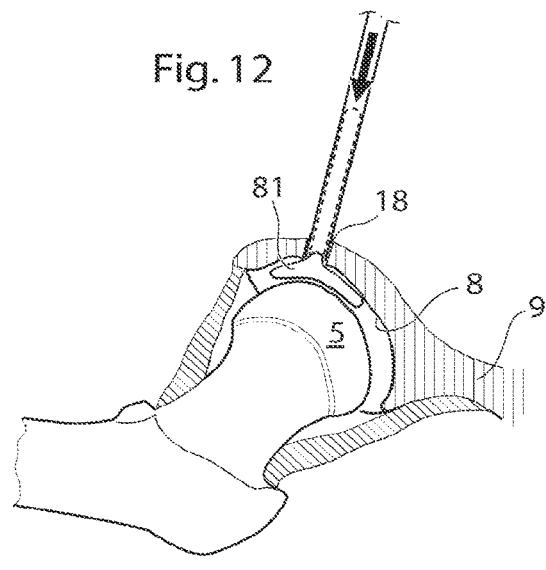
FIG. 12 shows the insertion of a mould.

FIG. 12 shows the step of placing a mould 81 inside of the hip joint of a human patient through a hole 18 in the pelvic bone 9. The step of placing said mould 81 can be performed in a surgical, or in a laparoscopic/arthroscopic method.

Figure 13:
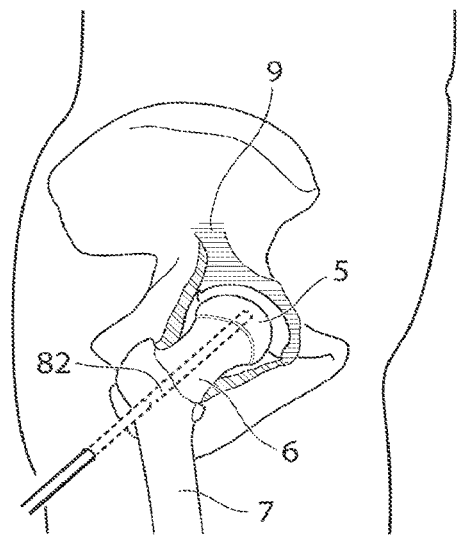
FIG. 13a shows the insertion of a mould.
FIG. 13b shows the insertion of a mould.
FIG. 13c shows the filling of a mould.
FIG. 13d shows the hip joint in section after the mould has been filled.
Figure 13:
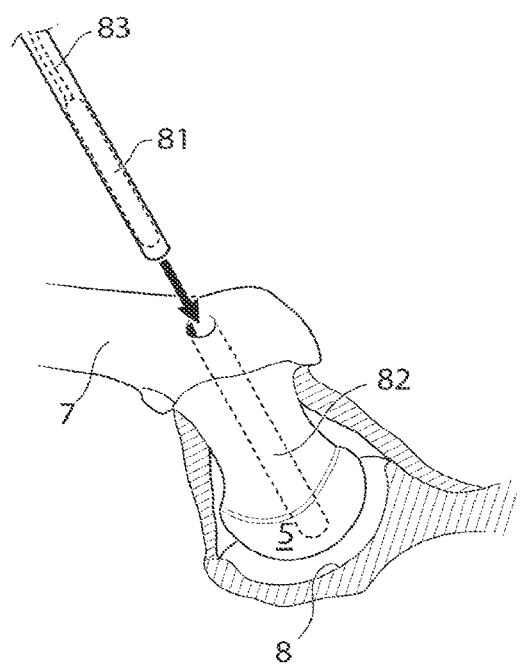
Figure 13:
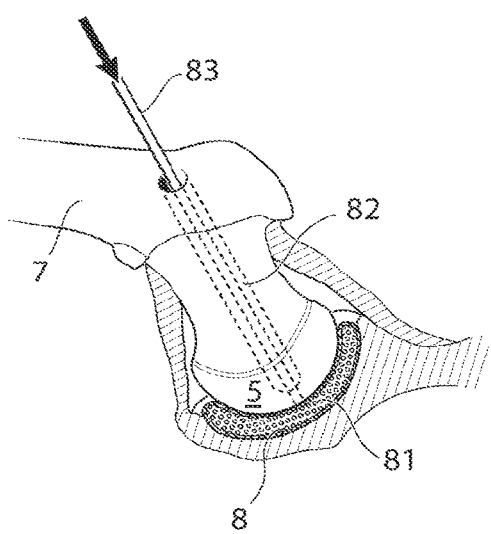
Figure 13:
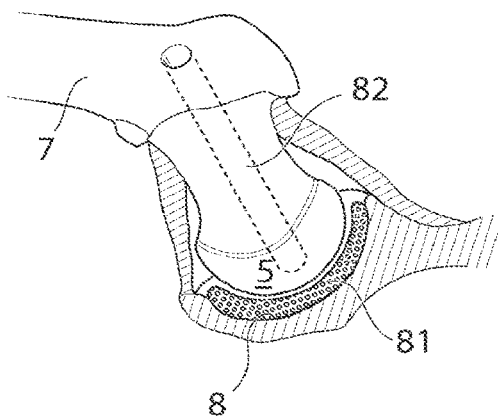

FIG. 13a,b,c,d shows an alternative approach to placing said mould 81 in the hip joint of a human patient. Said alternative approach comprises the steps of creating a hole 82 in the femur bone 7 following a length axis of the collum femur 6, said hole starting from the lateral side of the thigh, penetrating the cortex of the femur bone 7 and eventually reaching the cortex of the caput femur 5 from the inside thereof, penetrating said cortex and entering into the hip joint. After the creation of the hole 82 in the femur bone 7 the mould 81 is inserted into the hip joint through the hole 82 using the surgical instrument 83 according to any of the embodiments above, as shown in FIG. 13b.

FIG. 13c shows the mould 81 when being inserted into the hip joint using the surgical instrument 83 adapted therefore.

FIG. 13d shows the mould 81 in place after insertion into the hip joint, the surgical instrument used to place said mould 81 in the hip joint is retracted after the insertion is completed.

Figure 14:
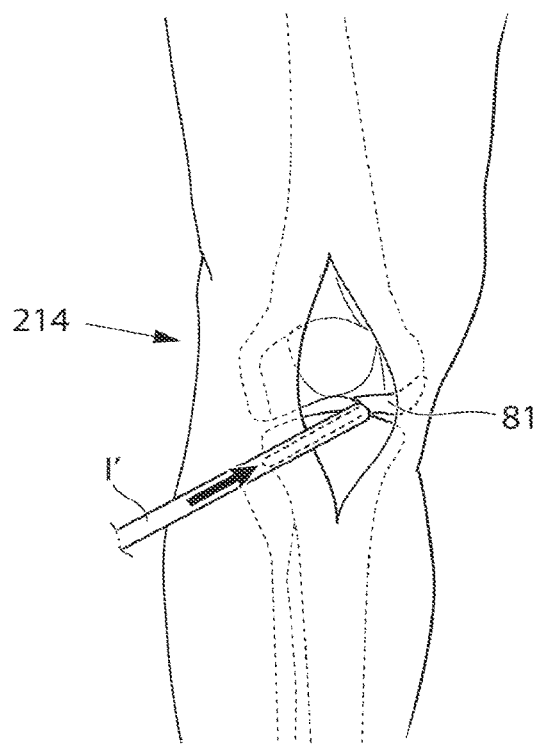
FIG. 14 shows the placing of a mould in the knee joint.

FIG. 14 shows the placing of a mould 81 in a knee 214 in a surgical method. The mould 81 is placed using the surgical instrument according to any of the embodiments above.

Figure 15:
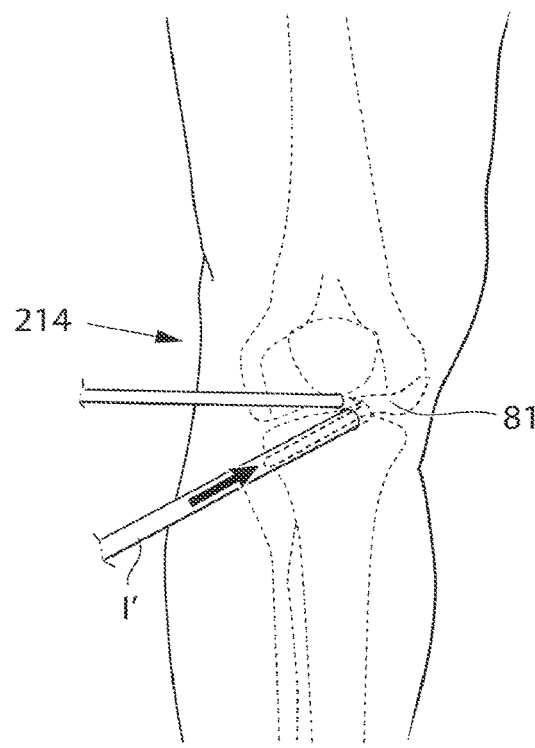
FIG. 15 shows the placing of a mould in the knee joint.

FIG. 15 shows the placing of a mould 81 in a knee 214 in a laparoscopic/arthroscopic method. The mould 81 is placed using the surgical instrument according to any of the embodiments above.

After the mould has been placed in the hip or knee joint it is filled with a fluid adapted to harden to a medical device adapted to serve as at least one artificial joint surface.

Figure 16:
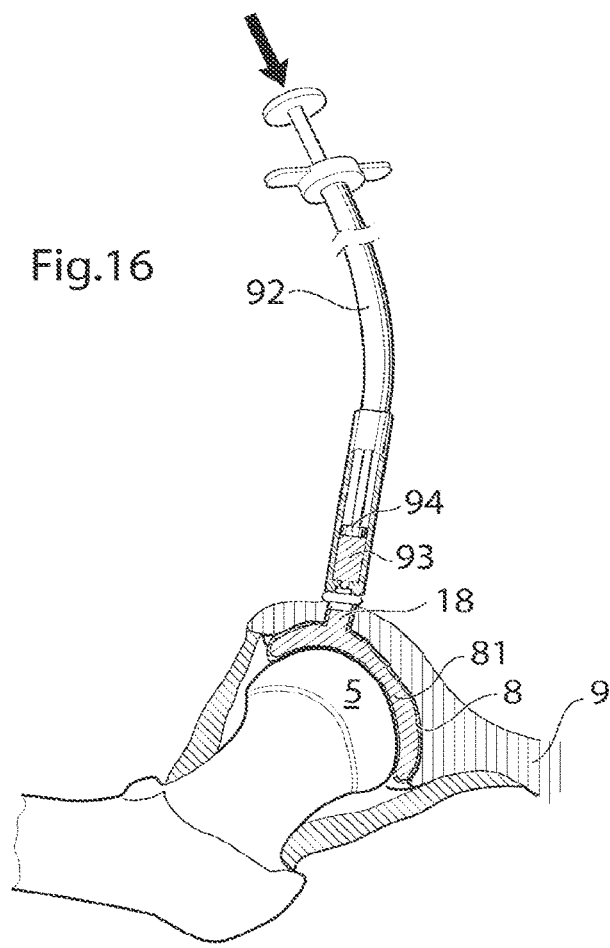
FIG. 16 shows the filling of a mould in the hip joint.

FIG. 16 shows the hip joint in section wherein an injecting member 92 injects a fluid 93 into a mould 81 in the hip joint through a hole 18 in the pelvic bone 9 from the opposite side from acetabulum 8. The injecting member 92 comprises a piston 94 that pushes said fluid 93 into the mould 81.

Figure 17:
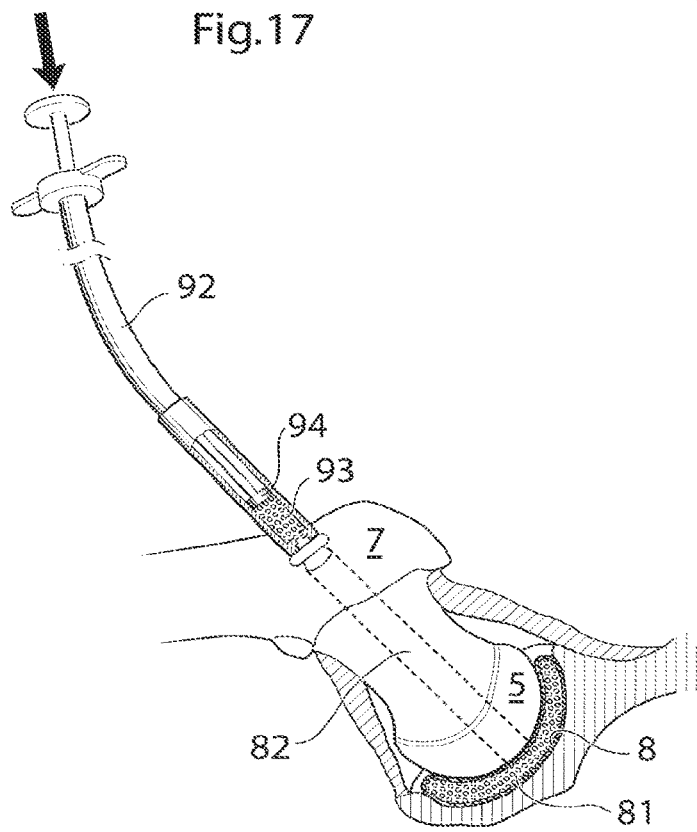
FIG. 17 shows the filling of a mould in the hip joint.

FIG. 17 shows the hip joint in section wherein an injecting member 92 injects a fluid 93 into a mould 81 in the hip joint through a hole 82 in the femur bone 7. The injecting member 92 comprises a piston 94 that pushes said fluid 93 into the mould 81.

Figure 18:
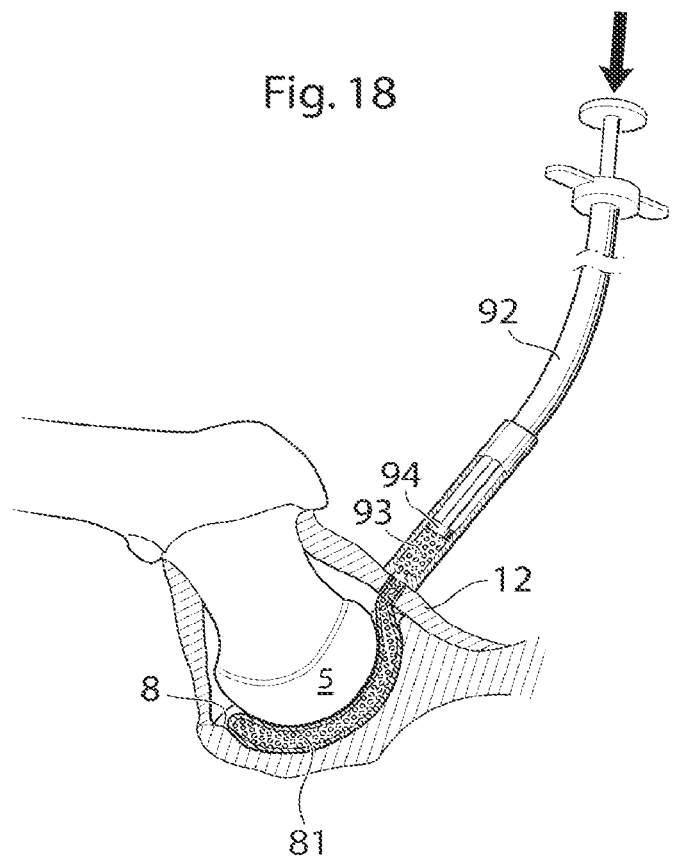
FIG. 18 shows the filling of a mould in the hip joint.

FIG. 18 shows the hip joint in section, wherein an injecting member injects a fluid 93 into a mould 81 in the hip joint through a hole in the hip joint capsule 12. The injecting member 92 comprises a piston 94 that pushes said fluid 93 into the mould 81. The fluid 93 is adapted to harden to create a medical device adapted to serve as at least one artificial hip joint surface.

Figure 19:
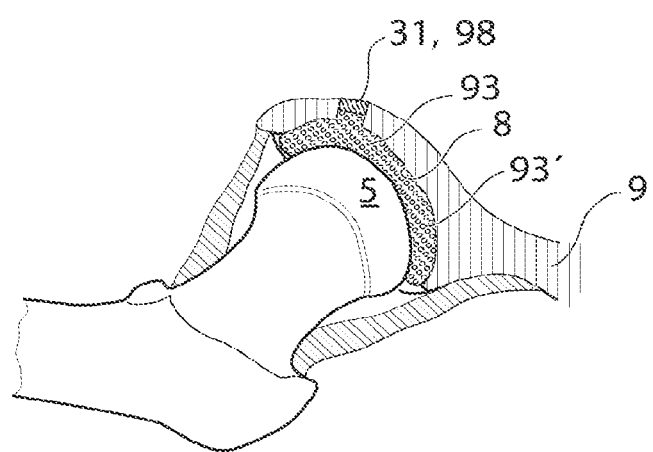
FIG. 19 shows the hip joint in section after the mould has been filled.

FIG. 19 shows the hip joint in section wherein the medical device 93' is located between the acetabulum 8 and the caput femur 5 which has been created by the hardening of the fluid 93 adapted to harden. Said medical device is adapted to serve as at least one artificial hip joint surface. The hole in the pelvic bone is preferably sealed with a bone plug 31 or a prosthetic part 98. The mould 81 used to create the medical device 93' has been removed.

Figure 20:
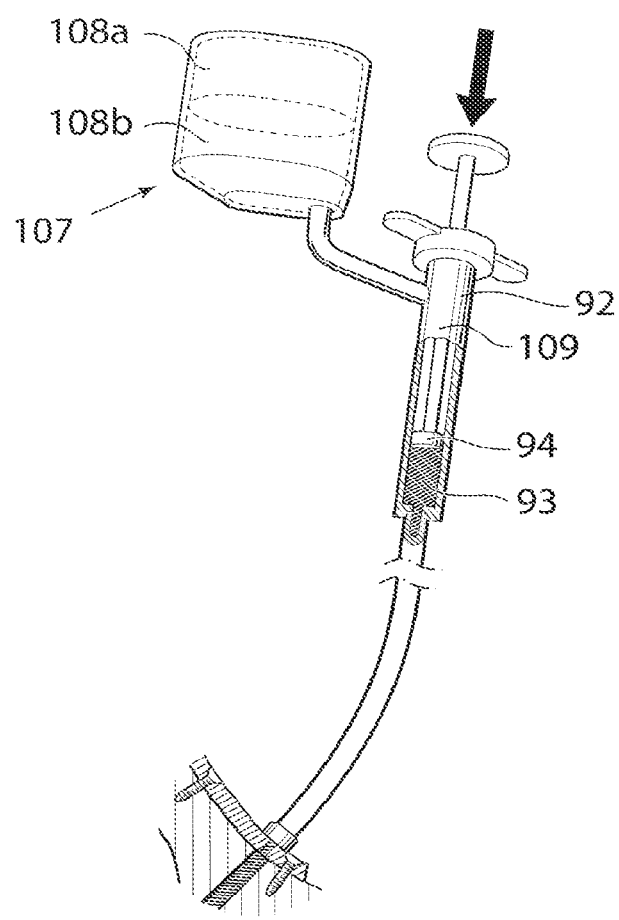
FIG. 20 shows a medical device for injecting a fluid.

FIG. 20 shows the injecting member 92 according to any of the embodiments above, adapted to inject fluid 93 into a mould 81 in the hip joint or the knee joint. The injecting member 92 could further be adapted to inject material 93 or a fluid 93 into a connecting area between the pelvic bone 9 and a prosthetic part, the pelvic bone 9 and a bone plug 31 or the caput femur 5 and a prosthetic part. Said injecting member 92 comprises a container 107 adapted to hold a fluid 93 for injection. According to a first embodiment said container 107 comprises two compartments 108a,b adapted to hold two different fluids, said fluids being adapted to harden when mixed. In the embodiment when the container 107 is adapted to hold two fluids, it is conceivable that the injecting member 105 further comprises a mixing member 109 wherein said two fluids are being mixed before injection. According to a second embodiment (not shown) said container 107 is adapted to keep said fluid sterile. According to a third embodiment (not shown) said container 107 is adapted to keep said fluid cold or hot and according to a fourth embodiment (not shown) said container 107 is adapted to keep said fluid in a dark environment. Furthermore a combination of the above mentioned embodiments is conceivable.

The term "comprises/comprising" when used in this specification is taken to specify the presence of stated features, integers, steps or components. However, the term does not preclude the presence or addition of one or more additional features, integers, steps or components or groups thereof.

The reference to any prior art in this specification is not, and should not be taken as, an acknowledgement or any suggestion that the referenced prior art forms part of the common general knowledge in Australia, or in any other country.

The invention is not restricted to the described embodiments in the figures, but may be varied freely within the scope of the claims.

The invention claimed is:

1. A method for treatment of arthrosis in a joint of a mammal or human patient, the method comprising:
    feeding a volume of a biocompatible material in liquid form into a reservoir (110) located outside of a body containing a joint (J) to be treated,
    inserting into the joint (J) an instrument (120) having a general tube shape, a distal end (D) of the instrument (120) being configured to be inserted into the joint (J), and a proximal end (P) of the instrument (120) being connected to the reservoir (110),
        receiving the liquid material from the reservoir (110) in the instrument (120),
        feeding the liquid material from the proximal end (P) to the distal end (D) of the instrument (120), and
    deposing the material on at least one damaged surface (S) of the joint (J), the material being configured to assume a solid form under predefined conditions, and when in the solid form the material having a resistance to wear adapted to replace a worn out joint surface, wherein said biocompatible material has a temperature higher than 90° C. when entering the joint.

2. The method according to claim 1, further comprising:
    inserting a mould member (140) into the joint (J), the mould member (140) having a pre-produced shape adapted to a shape and size of at least one of the at least one damaged surface (S) so as contact and cover this surface (S) when placed in the joint (J), the mould member (140) being flexible, collapsible and having an internal volume configured to be filled with liquid material received via the instrument (120), the mould member (140) being connected to the distal end (D) of the instrument (120),
    form-fitting the mould member (140) to said at least one damaged surface (S),
    injecting the material into the mould member (140) through the instrument (120), receiving the material in the mould member (140), causing a transition of the material from the liquid form to the solid form after that the mould member (140) has been filled with the liquid material.

3. The method according to claim 2, comprising pre-producing the mould member (140) according to a shape and size of at least one of the damaged surface (S) so as enable the mould member (140) to contact and cover the damaged surface (S) when placed in the joint (J).

4. The method according to claim 3, comprising determining the shape and size of the at least one of the damaged surface (S) via a magnetic resonance imaging investigation, a computer tomography x-ray investigation or via arthroscopy.

5. The method according to claim 2, comprising illuminating the joint (J) by means of a light source (130) during deposition of the liquid material on at least one damaged surface (S) of the joint (J).

6. The method according to claim 2, wherein the biocompatible liquid material comprises fluoropolymers.

7. The method according to claim 6, wherein the fluoropolymers comprises one of polytetrafluoroethylene, perfluoroalkoxy or fluorinated ethylene propylene.

8. The method according to claim 1, wherein the biocompatible material comprises two components, each component when isolated from the other component being a liquid, the components when mixed in predefined proportions developing a solid material, the reservoir (110) being configured to hold the two components separated from one another, and the method comprising:
    mixing the two components during surgery, and subsequently
    feeding the mixed components through the instrument (120) to the at least one damaged joint surface (S).

9. The method according to claim 1, wherein the biocompatible material is liquid when exposed to electromagnetic radiation in a predefined spectrum being below a first predefined energy level per unit volume, and the biocompatible material is a solid material when exposed to electromagnetic radiation in the predefined spectrum above a second predefined energy level per unit volume, and the method comprising irradiating the at least one damaged joint surface (S) with electromagnetic radiation in the predefined spectrum.

10. The method according to claim 1, wherein the biocompatible material is liquid when exposed to ultrasonic energy in a predefined spectrum being below a primary predefined energy level per unit volume, and the biocompatible material is a solid material when exposed to ultrasonic energy in the predefined spectrum being above a secondary predefined energy level per unit volume, and the method comprising sending ultrasonic energy in the predefined spectrum to the at least one damaged joint.

11. The method according to claim 1, comprising maintaining the biocompatible material sterile in the reservoir (110) and in a connection to the instrument (120).

12. The method according to claim 1, comprising inserting the distal end (D) of the instrument (120) into the joint (J) via at least one bone (210, 220) of the body.

13. The method according to claim 1, comprising inserting the distal end (D) of the instrument (120) into a hip joint (J) by passing via a bone (220) of the body from inside the abdomen.

14. The method according to claim 1, comprising inserting the distal end (D) of the instrument (210) into a hip joint (J) by passing via the femoral bone (210) of the body.

15. The method according to claim 1, comprising inserting the distal end of the instrument (120) into the joint (J) by passing via a capsula of the joint (J).

16. The method according to claim 1, comprising the biocompatible material at a temperature of at least 150 degrees Celsius in the reservoir (110), or of at least 200 degrees Celsius in the reservoir, or of at least 300 degrees Celsius in the reservoir, or of at least 400 degrees Celsius in the reservoir.

17. The method according to claim 1, wherein said material comprises at least one material selected from the group consisting of:
   polytetrafluoroethylene,
   perfluoroalkoxy
   fluorinated ethylene propylene,
   polyethylene, and
   acrylic polymer mixed with alumina trihydrate.

* * * * *